United States Patent
Hanada et al.

(10) Patent No.: US 10,524,994 B2
(45) Date of Patent: Jan. 7, 2020

(54) CONDITIONING AGENT AND CONDITIONING COMPOSITION

(71) Applicant: Kokyu Alcohol Kogyo Co., Ltd., Narita-shi, Chiba (JP)

(72) Inventors: Naomi Hanada, Narita (JP); Takayuki Omura, Narita (JP)

(73) Assignee: Kokyu Alcohol Kogyo Co., Ltd., Narita-shi, Chiba (JP)

( * ) Notice: Subject to any disclaimer, the term of this patent is extended or adjusted under 35 U.S.C. 154(b) by 0 days.

(21) Appl. No.: 16/155,982

(22) Filed: Oct. 10, 2018

(65) Prior Publication Data

US 2019/0125645 A1    May 2, 2019

(30) Foreign Application Priority Data

Nov. 1, 2017 (JP) .................................. 2017-211830

(51) Int. Cl.
| | |
|---|---|
| *A61K 8/42* | (2006.01) |
| *A61K 8/44* | (2006.01) |
| *A61Q 5/12* | (2006.01) |
| *A61Q 19/00* | (2006.01) |
| *A61K 8/06* | (2006.01) |
| *A61K 8/31* | (2006.01) |

(52) U.S. Cl.
CPC ............... *A61K 8/42* (2013.01); *A61K 8/062* (2013.01); *A61K 8/31* (2013.01); *A61K 8/44* (2013.01); *A61Q 5/12* (2013.01); *A61Q 19/00* (2013.01); *A61K 2800/33* (2013.01)

(58) Field of Classification Search
None
See application file for complete search history.

(56) References Cited

U.S. PATENT DOCUMENTS

| | | | |
|---|---|---|---|
| 3,647,738 A * | 3/1972 | Foster | .............. C07C 233/00 524/224 |
| 4,325,973 A | 4/1982 | Graham et al. | |
| 6,271,327 B1 | 8/2001 | Niessner et al. | |
| 2001/0053828 A1 | 12/2001 | Nishiguchi et al. | |
| 2003/0147822 A1 | 8/2003 | Doi et al. | |
| 2005/0037934 A1 | 2/2005 | Inoue et al. | |
| 2006/0046286 A1 | 3/2006 | Watanabe | |
| 2006/0150344 A1 | 7/2006 | Muller et al. | |
| 2016/0220469 A1 | 8/2016 | Baghdadli et al. | |
| 2017/0281494 A1 | 10/2017 | Haraya et al. | |

FOREIGN PATENT DOCUMENTS

| | | |
|---|---|---|
| DE | 1920975 A1 | 11/1969 |
| EP | 0621265 A1 | 10/1994 |
| EP | 0704200 A1 | 4/1996 |
| EP | 1181925 A2 | 2/2002 |
| FR | 2855049 A1 | 11/2004 |
| FR | 3010309 A1 | 3/2015 |
| JP | H06-178928 A | 6/1994 |
| JP | H09-278728 A | 10/1997 |
| JP | 2000-234077 A | 8/2000 |
| JP | 2000-515916 A | 11/2000 |
| JP | 2002-285469 A | 10/2002 |
| JP | 2003-171358 A | 6/2003 |
| JP | 2004-2261 A | 1/2004 |
| JP | 2005-053823 A | 3/2005 |
| JP | 2006-063001 A | 3/2006 |
| JP | 2007-503379 A | 2/2007 |
| JP | 2015-067571 A | 4/2015 |
| WO | WO 2002/055053 A2 | 7/2002 |
| WO | WO 2016/104697 A1 | 6/2016 |

OTHER PUBLICATIONS

Foster, George N., SciFinder abstract (CAPLUS Acc. No. 1972:154764) of U.S. Pat. No. 3,647,738 A (Mar. 7, 1972), accessed online on May 1, 2019, copyright 2019 to the American Chemical Society (ACS).*
EP 18202772, Feb. 21, 2019, European Search Report.

* cited by examiner

*Primary Examiner* — Brian J Davis
(74) *Attorney, Agent, or Firm* — Wolf, Greenfield & Sacks, P.C.

(57) ABSTRACT

[Problem] An object of the invention is to provide a conditioning agent and a conditioning composition which are excellent in adsorptivity to fibers, hair, skin, etc. and impart smoothness thereto.
[Solving means] A conditioning agent comprising an amide alcohol represented by formula (I).

10 Claims, 2 Drawing Sheets

Fig. 1
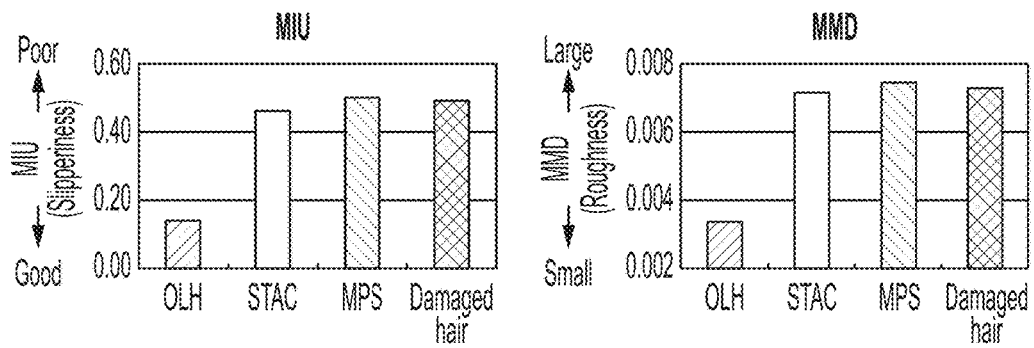
Fig. 2
|  | Amide alcohol OLH | STAC | MPS |
|---|---|---|---|
| Surface observation image (x2000) | D500:X2000 | D500:X2000 | D500:X2000 |
| Adsorptivity | A | C | C |
Fig. 3
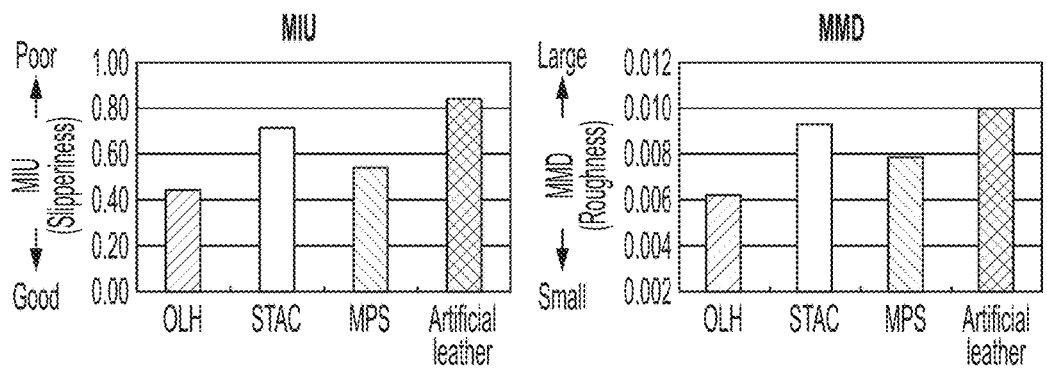

CONDITIONING AGENT AND CONDITIONING COMPOSITION

TECHNICAL FIELD

The present invention relates to a conditioning agent and a conditioning composition.

BACKGROUND ART

Conventionally, various cationic surfactants have been used to impart flexibility to fibers and hair (Patent Documents 1 and 2). However, cationic surfactants have problems such as skin irritation and adverse effects on the environment due to their poor biodegradability. It has been proposed to use amidoamines for remedying such problems (Patent Documents 3 to 6), however, adsorptivity and smoothness are not sufficient.

Incidentally, amide alcohols are known as an oil gelling agent (Patent Document 7); however, their conditioning effect has not been known.

CITATION LIST

Patent Document

[Patent Document 1] JP A H06-178928
[Patent Document 2] JP A 2002-285469
[Patent Document 3] JP A H09-278728
[Patent Document 4] JP A 2003-171358
[Patent Document 5] JP A 2004-2261
[Patent Document 6] WO 2016/104697

DISCLOSURE OF INVENTION

Problems to be Solved by the Invention

In view of the above-mentioned problems in the prior art, an object of the present invention is to provide a conditioning agent which has high adsorptivity and imparts smoothness to fibers, hair and skin. In particular, it is an object of the present invention to provide a conditioning agent which imparts excellent smoothness to hair.

Another object of the present invention is to provide a conditioning composition such as softening agent and conditioner.

It is a further object of the present invention to provide a conditioning composition in a stable emulsified state.

Means for Solving the Problems

During extensive research to solve the above problems, the present inventors have found that a specific amide alcohol has a conditioning effect; and as a result of further research, the inventors have completed the present invention.

That is, the present invention relates to the following [1] to [13].

[1] A conditioning agent comprising an amide alcohol represented by formula (I):

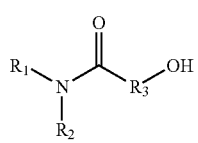

wherein
R$_1$ is a C6-C22 hydrocarbon group which may be substituted,
R$_2$ is H, or a C6-C22 hydrocarbon group which may be substituted,
R$_3$ is a linear or branched C2-C21 hydrocarbon group which may be substituted.

[2] The conditioning agent according to [1], comprising the amide alcohol represented by formula (I), wherein
R$_1$ is a C10-C22 hydrocarbon group,
R$_2$ is H,
R$_3$ is a C3-C12 hydrocarbon group.

[3] The conditioning agent according to [1] or [2], wherein the amide alcohol is:

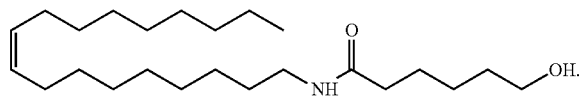 [SMILES: CCCCCCCC/C=C\CCCCCCCCNC(=O)CCCCCO]

[4] A conditioning composition comprising an organic acid and an amide alcohol represented by formula (I):

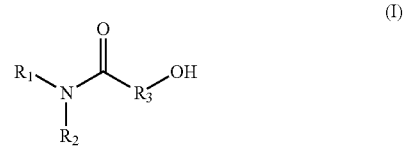

wherein
R$_1$ is a C6-C22 hydrocarbon group which may be substituted,
R$_2$ is H, or a C6-C22 hydrocarbon group which may be substituted,
R$_3$ is a linear or branched C2-C21 hydrocarbon group which may be substituted.

[5] The composition according to [4], comprising:
0.1 to 10.0 mass % of the amide alcohol represented by formula (I), and
0.1 to 10.0 mass % of the organic acid.

[6] The composition according to [4] or [5], wherein the molar ratio of the amide alcohol represented by formula (I) to the organic acid is from 2:1 to 1:1.

[7] The composition according to any one of [4] to [6], wherein the organic acid is one or more selected from the group consisting of a monocarboxylic acid, a dicarboxylic acid, a hydroxycarboxylic acid, a polycarboxylic acid, an acidic amino acid, and a fatty acid.

[8] The composition according to any one of [4] to [7], comprising one or more oil agents selected from the group consisting of ester oils, silicone oils, and hydrocarbon oils.

[9] The composition according to [8], which is an O/W emulsion composition.

[10] The composition according to [9], which is substantially free of surfactant.

[11] The composition according to any one of [4] to [10], comprising glutamic acid as the organic acid.

[12] The composition according to any one of [8] to [11], comprising one or more selected from the group consisting of squalane, liquid paraffin, and/or nonvolatile hydrocarbon oil as the oil agent.

[13] The composition according to any one of [4] to [12], which is hair and/or skin cosmetics.

Advantageous Effects of Invention

The present invention provides, by using a specific amide alcohol, a conditioning agent which has high adsorptivity to fibers, hair and skin and imparts smoothness thereto.

Furthermore, by combining said conditioning agent and an organic acid, the present invention provides a conditioning composition which can be used as a softening agent for fibers and as a conditioner for skin and/or hair.

BRIEF DESCRIPTION OF DRAWINGS

FIG. 1 is a graph showing smoothness (slipperiness and roughness) on the hair.
FIG. 2 is a diagram showing adsorption to the hair.
FIG. 3 is a graph showing smoothness (slipperiness and roughness) on the skin.

DESCRIPTION OF EMBODIMENTS

Component (A): Amide Alcohol

Figure 4:
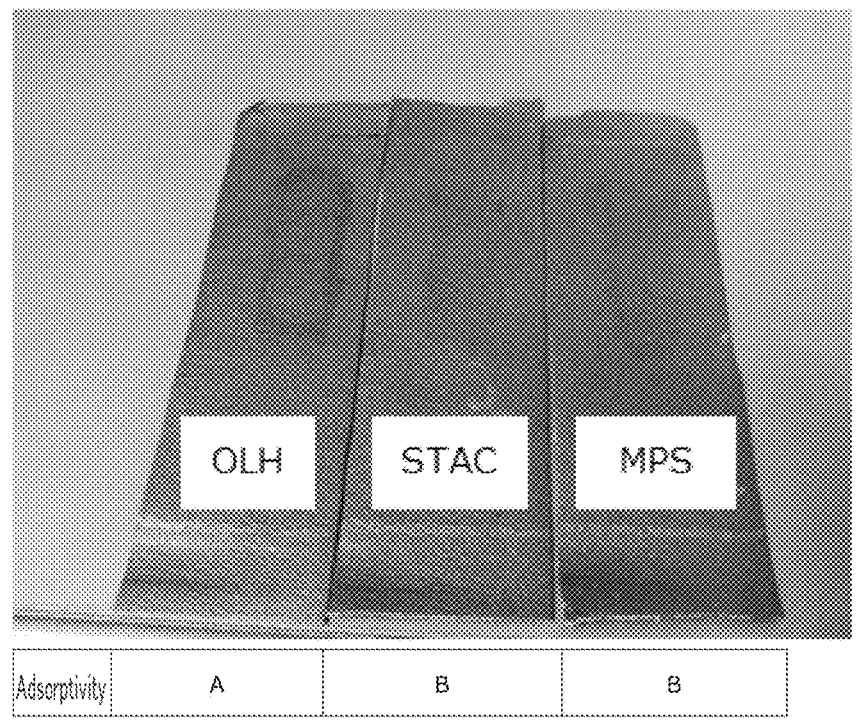
FIG. 4 is a diagram showing adsorption to the skin.

The amide alcohol used in the present invention is represented by the following formula (I):

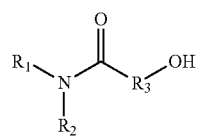

(I)

wherein
$R_1$ is a C6-C22 hydrocarbon group which may be substituted,
$R_2$ is H, or a C6-C22 hydrocarbon group which may be substituted,
$R_3$ is a linear or branched C2-C21 hydrocarbon group which may be substituted.

As used herein, the term "hydrocarbon group" may be saturated or unsaturated, linear or branched or cyclic, or a combination of linear or branched with cyclic, unless otherwise specified, and includes a hydrocarbon group consisting of a linear or branched hydrocarbon moiety such as benzyl group, phenylethyl group, and a cyclic hydrocarbon moiety.

That is, the C6-C22 hydrocarbon group in $R_1$ and $R_2$ includes a linear, branched or cyclic C6-C22 hydrocarbon group, or a C6-C22 hydrocarbon group consisting of a linear or branched hydrocarbon moiety and a cyclic hydrocarbon moiety, and examples thereof include cyclic groups such as cyclohexyl, decahydronaphthyl, tetrahydrodicyclopentadiene, sterol, phenyl, naphthyl, anthracenyl; branched alkyl groups such as ethylhexyl, isostearyl, octyldodecyl; multi-branched alkyl groups such as dimethyl, trimethyl, tetramethyl; linear alkyl groups such as hexyl, octyl, lauryl, myristyl, cetyl, stearyl, arachyl, behenyl; and alkenyl groups such as oleyl and elaidyl.

In one embodiment of the present invention, $R_1$ is preferably an unsubstituted hydrocarbon group. Specifically, it is preferably an unsaturated linear or branched C10-C22 hydrocarbon group; or a cyclic C6-C22 hydrocarbon group; or a benzyl group or phenylethyl group.

Specific examples of $R_1$ include cyclohexyl, ethylhexyl, octyl, lauryl, myristyl, stearyl, oleyl, benzyl or phenylethyl.

In one embodiment of the present invention, $R_1$ is particularly preferably lauryl, myristyl, stearyl and oleyl.

In one embodiment of the present invention, $R_2$ is preferably H.

The hydrocarbon group in $R_3$ is a linear or branched C2-C21 hydrocarbon group having no cyclic structure, and examples thereof include alkyl groups such as propyl, butyl, pentyl, hexyl, heptyl, octyl, ethylhexyl, and alkenyl groups such as butylene, pentylene, hexylene, heptylene.

In one embodiment of the present invention, $R_3$ is a linear or branched C2-C12 hydrocarbon group, preferably an alkyl group, and specifically it is preferably propylene, butylene, pentylene or hexylene.

In the present invention, each hydrocarbon group may be substituted, and may be substituted with, for example, a hydroxy group, a carboxy group, and an aldehyde group.

Examples of substituted C6-C22 hydrocarbon groups in $R_1$ and $R_2$ include hexanol, ethylcyclohexanol, and hexanoic acid.

Examples of substituted C2-C21 hydrocarbon groups in $R_3$ include hydroxybutyl, and butyl ketone.

In one embodiment of the present invention, an amide alcohol of formula (I) wherein $R_1$ is a C10-C22 hydrocarbon group, $R_2$ is H, and $R_3$ is a C3-C12 hydrocarbon group is preferred, and particular preference is given to the amide alcohol of formula (I) wherein $R_1$ is a C12-C18 hydrocarbon group, $R_2$ is H, and $R_3$ is a C3-C5 hydrocarbon group.

In a preferred embodiment of the present invention, the amide alcohol of formula (I) has a structure of:

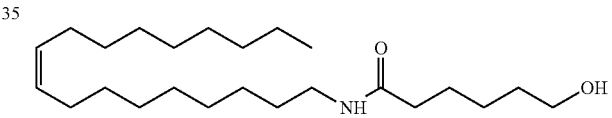

Amide alcohols can be prepared using known synthetic methods.

Examples include:
aminolysis reaction of acid chloride and amine (Schotten-Baumann reaction),
aminolysis reaction of anhydrous fatty acid and amine,
aminolysis reaction of methyl ester and amine,
aminolysis reaction of fatty acid and amine,
aminolysis reaction of lactone and amine,
and the like.

Specifically, for example, it can be synthesized by a method described in Japanese Patent Application No. 2016-114276 (JP 6247340 B, registered on Nov. 24, 2017 and published on Dec. 13, 2017).

In the present specification, "conditioning" means imparting smoothness/slipping property and flexibility to fibers, hair, skin, etc.

In the present specification, "conditioning agent" means an ingredient used for providing a conditioning effect to a composition such as daily necessities and cosmetics.

The conditioning agent of the present invention may consist solely of the amide alcohol represented by formula (I) or may comprise further components.

Although not bound by any theory, it is considered that the amide alcohol represented by formula (I) has high adsorptivity by having a nitrogen atom, and has a characteristic of adsorbing to fibers, hair and skin surfaces.

In the present specification, "conditioning composition" means a composition used for conditioning, and includes a product for textile, clothing and fabric such as softening agent and styling agent for clothing; hair cosmetics such as hair conditioner, hair treatment, and hair styling agent; skin cosmetic products including skin care cosmetics such as gel lotion, milky lotion, cream, beauty essence, sunscreen, and daytime moisturizer, as well as make-up cosmetics such as foundation, make-up base, eye shadow, mascara.

The conditioning composition contains an amide alcohol represented by formula (I) and an organic acid.

In the present invention, by using the amide alcohol represented by formula (I), it is possible to impart high adsorptivity to compositions.

In one embodiment of the present invention, the blending amount of the amide alcohol represented by formula (I) in the conditioning composition is not particularly limited; from the viewpoint of giving a sufficient conditioning effect, it may be 0.1 to 10.0 mass %, preferably 0.1 to 8.0 mass %, and more preferably 0.1 to 5.0 mass %.

In one embodiment of the present invention, pH can be adjusted by using an organic acid.

In one embodiment of the present invention, the conditioning composition can be emulsified by using an organic acid.

In one embodiment of the present invention, the blending amount of the organic acid in the conditioning composition is not particularly limited; from the viewpoint of pH adjustment, it may be 0.1 to 10.0 mass %, more preferably 0.1 to 5.0 mass %, and more preferably 0.1 to 3.0 mass %.

In a particular embodiment of the present invention, the conditioning composition is an O/W emulsion composition.

The organic acid used in the conditioning composition is not particularly limited as long as it is a component generally used in a conditioning composition; examples of which include monocarboxylic acids such as acetic acid, propionic acid; dicarboxylic acids such as malonic acid, succinic acid, glutaric acid, adipic acid, maleic acid, fumaric acid, phthalic acid; hydroxycarboxylic acids such as glycolic acid, lactic acid, hydroxyacrylic acid, glyceric acid, malic acid, tartaric acid, citric acid; polycarboxylic acids such as polyglutamic acid; acidic amino acids such as glutamic acid, aspartic acid; fatty acids such as lauric acid, myristic acid, palmitic acid, stearic acid, isostearic acid, oleic acid, erucic acid, behenic acid, dimer acid, hydroxystearic acid, castor oil fatty acid; and these can be used alone or in combination of two or more kinds.

As one embodiment of the present invention, from the viewpoint of obtaining a stable emulsion, it is preferable that the organic acid is glutamic acid or aspartic acid.

In one embodiment of the present invention, from the viewpoint of obtaining a stable emulsion, the molar ratio of the amide alcohol represented by formula (I) and the organic acid is preferably in the range of 2:1 to 1:1.

The conditioning composition of the present invention may further comprise an oil agent.

The oil agent used in the conditioning composition is not particularly limited as long as it is a component generally used in a conditioning composition; examples of which include oil agents such as animal and vegetable fats and oils, hydrocarbon oils, higher fatty acids, higher alcohols, ester oils, silicone oils; and these can be used alone or in combination of two or more kinds.

In one embodiment of the present invention, from the viewpoint of obtaining a stable emulsion, it is preferable that the oil agent is ester oil, silicone oil or hydrocarbon oil.

In one embodiment of the present invention, from the viewpoint of obtaining a stable emulsion, it is preferable that the oil agent is squalane, liquid paraffin and/or nonvolatile hydrocarbon oil.

<Other Components>

The conditioning composition of the present invention may include any components used for textile, clothing and fabric products sued as softening agents, or for cosmetics such as hair conditioners.

Examples of these additional components include surfactants; humectants such as 1,3-butylene glycol, propylene glycol, glycerin; ultraviolet absorbing agents such as ethylhexyl methoxycinnamate, hexyl diethylaminohydroxybenzoylbenzoate; thickeners/gelling agents such as dextrin palmitate, xanthan gum; quality maintaining components such as antioxidant, and preservative; medicinal components and active components such as whitening agent, anti-wrinkle agent, antioxidative agent; coloring agents; fragrances.

In one embodiment of the present invention, the conditioning composition is substantially free of surfactant such as cationic surfactant.

Here, "surfactant" means a compound having both a hydrophilic group and a hydrophobic group in one molecule. In addition, in the present invention, "substantially free of surfactant" means that it comprises no surfactant at all or comprises a surfactant in an amount that does not emulsify. The amount that does not emulsify can be appropriately determined by a person skilled in the art according to the compositional ratio, for example, in one embodiment it is less than 2.0 mass %, in another embodiment it is less than 0.2 mass %, or less than 0.02 mass %.

In a particular embodiment of the invention, the conditioning composition is an O/W emulsion composition substantially free of surfactant such as cationic surfactant.

Hereinafter, the present invention will be described in more detail based on examples; however, the present invention is not limited to these examples, and various modifications can be made without departing from the technical idea of the present invention. In the present specification, unless otherwise specified, % means mass %.

EXAMPLE

Test Example 1

Treatments of the formulation in Table 1 were prepared using, as a conditioning agent, an amide alcohol having the following structure (hereinafter also referred to as amide alcohol OLH):

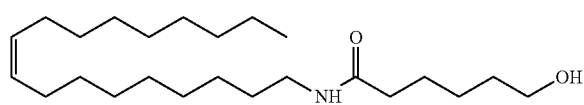 [SMILES: CCCCCCCC/C=C\CCCCCCCCNC(=O)CCCCCO]

or a cationic surfactant steartrimonium chloride (STAC), stearamidopropyl dimethylamine (MPS).

TABLE 1

Formulation of treatments

| | | Example 1 | Comparative Example 1 | Comparative Example 2 |
|---|---|---|---|---|
| Oil phase | Squalane | 12.0 | 12.0 | 12.0 |
| | Amide alcohol OLH | 3.0 | — | — |
| | Steartrimonium chloride | — | 3.0 | — |
| | Stearamidopropyl dimethylamine | — | — | 3.0 |
| | Cetostearyl alcohol | 3.0 | 3.0 | 3.0 |
| | DPG | — | 2.0 | — |
| Aqueous phase | Glycerin | 3.0 | 3.0 | 3.0 |
| | Glutamic acid | 0.6 | 0.6 | 0.6 |
| | Water | 78.4 | 76.4 | 78.4 |
| Feeling of use (evaluation) | Moisturizing feeling | A | C | C |
| | Settled feeling | A | C | C |
| | Smoothness | A | C | C |

[Manufacture]

Oil phase components are uniformly dissolved at 80° C. Next, aqueous phase components are uniformly dissolved at 80° C. While stirring the oil phase at 80° C., the aqueous phase is gradually added and emulsified. It was cooled to room temperature while stirring, to obtain a treatment.

<Conditioning Effect on the Hair>
[Evaluation of Feeling of Use]

Regarding the evaluation of feeling of use on hair, after washing the hair with a shampoo, each treatment was applied, rinsed off, and the hair was dried with towel and then with a dryer; the feeling of use was sensory-evaluated by ten panelists based on the feeling such as hand feel of the hair.

Based on 5 grades (5: very good, 4: good, 3: normal, 2: poor, 1: very poor), the average was calculated and ranked as follows.

<Moisturizing Feeling after Shampooing>
A: Moisturizing (average of 4.0 or more in 5 grades)
B: Slightly moisturizing (average of 2.5 to 4.0 in 5 grades)
C: Not moisturizing/refreshing/dry, etc. (average of 2.5 or less in 5 grades)

<Settled Feeling of the Hair after Shampooing>
A: Easy to settle (average of 4.0 or more in 5 grades)
B: Slightly easy to settle (average of 2.5 to 4.0 in 5 grades)
C: Hard to settle/not settled (average of 2.5 or less in 5 grades)

<Smoothness after Shampooing>
A: Good smoothness (average of 4.0 or more in 5 grades)
B: Slightly good smoothness (average of 2.5 to 4.0 in 5 grades)
C: Poor smoothness (average of 2.5 or less in 5 grades evaluation)

The treatment containing the amide alcohol showed good results in all of the moisturizing feeling, settled feeling, and smoothness, after washing the hair.

[Evaluation of the Sense of Friction]

after washing the hair with a shampoo, each treatment was applied, rinsed off, and the hair was dried with towel and then with a dryer; the sense of friction of the hair was evaluated using Friction Tester KES-SE from Kato Tech Co., Ltd. The results are shown in FIG. 1.

The treatment containing the amide alcohol showed good results in terms of both slipperiness and roughness.

[Evaluation of Adsorptivity]

Regarding the adsorptivity to hair, after washing the hair with a shampoo, each treatment was applied, rinsed off, and the hair was dried with towel and then with a dryer; the condition of the hair was observed using a digital microscope VHX-2000 from Keyence Corporation. The results are shown in FIG. 2.

In the formulation containing the amide alcohol, adsorption on the hair surface was observed.

<Conditioning Effect on the Skin>
[Evaluation of the Sense of Friction]

Regarding the friction test of the skin, the above treatments were applied to artificial leather, spread five times, then washed with running water for about 15 seconds, and after wiping off the moisture with a paper towel, slipperiness/roughness were evaluated. As a device, Friction Tester KES-SE from Kato Tech Co., Ltd. was used. The results are shown in FIG. 3.

The treatment containing the amide alcohol showed good results also for the skin in terms of both slipperiness and roughness.

[Evaluation of Adsorptivity]

Regarding the adsorptivity to artificial leather, the appearance of the artificial leather after the above friction test was visually observed. The results are shown in FIG. 4.

It could be observed that the treatment remained on the surface of the artificial leather, and the highest adsorptivity was found for the treatment containing the amide alcohol.

Test Example 2

Using each of the amide alcohols listed in Table 2, treatments listed in Table 3 were prepared.

<Amide Alcohols Used>

TABLE 2

Amide alcohols used in Examples 2 to 4

| | Example 2 |
|---|---|
| Molecular weight | Amide alcohol MB<br>299.49 |
| Structural formula | [structure: long alkyl chain—NH—C(=O)—CH2CH2—OH] |

| | Example 3 |
|---|---|
| Molecular weight | Amide alcohol OLB<br>353.58 |
| Structural formula | [structure: long alkyl chain with double bond—NH—C(=O)—CH2CH2—OH] |

| | Example 4 |
|---|---|
| Molecular weight | Amide alcohol STB<br>355.6 |
| Structural formula | [structure: long alkyl chain—NH—C(=O)—CH2CH2—OH] |

TABLE 3

Formulation of Examples 2 to 4

| | | Product name/Cosmetic label name | wt % |
|---|---|---|---|
| Oil phase | 1. | Olive squalene (Squalane) | 6.0 |
| | 2. | Behenyl alcohol | 5.0 |
| | 3. | Amide alcohol | 3.0 |
| Aqueous phase | 4. | Triol VE (Glycerin) | 3.0 |
| | 5. | Lactic acid | 0.4 |
| | 6. | Purified water | 82.6 |

[Preparation Method]

The blending components of each phase were heated at 80° C. and dissolved. After uniformly dissolving, the oil phase was added to the aqueous phase and emulsified with a homomixer (3000 rpm, 3 min). Subsequently, the emulsion was cooled to 30° C. to obtain a treatment preparation.

[Evaluation]

Figure 5:
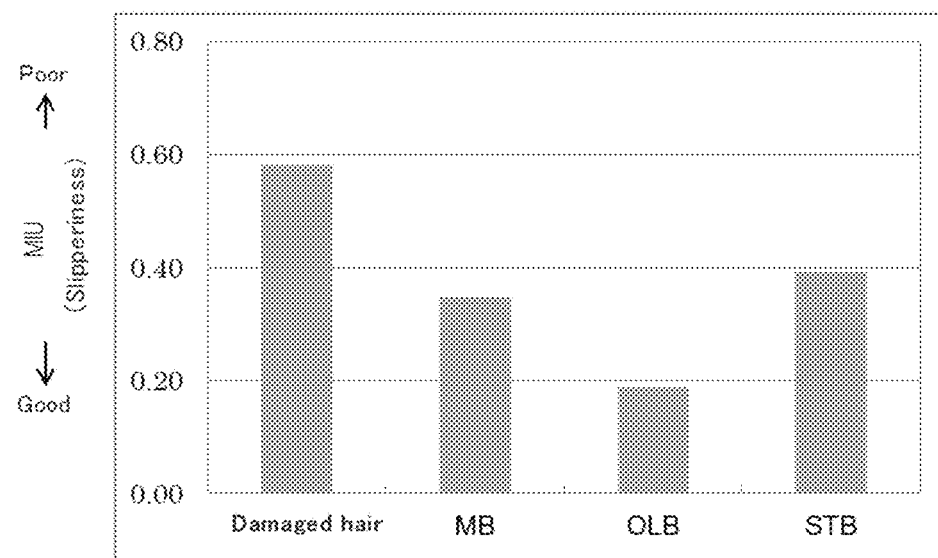
FIG. 5 is a graph showing slipperiness on the hair.

Sense of friction was evaluated in the same manner as in Test Example 1. The results are shown in FIG. 5.

The treatments containing various types of amide alcohols showed good slipping property.

Examples of each conditioning composition using an amide alcohol are described.

Example 5

Formulation of Hair Treatment

TABLE 4

| | | Blending amount (%) |
|---|---|---|
| (1) | Behenyl alcohol | 5.0 |
| (2) | Cetyl palmitate | 4.0 |
| (3) | Amide alcohol OLH | 2.5 |
| (4) | Isopropyl palmitate | 1.0 |
| (5) | Jojoba oil | 1.0 |
| (6) | Glyceryl stearate | 0.5 |
| (7) | Glycerin | 3.0 |
| (8) | Pentylene glycol | 2.0 |
| (9) | Hydroxyethyl cellulose | 0.3 |
| (10) | Glutamic acid | 0.5 |
| (11) | Hydrolyzed silk | 0.01 |
| (12) | Purified water | Balance |

(1) to (5) are uniformly dissolved at 80° C. (oil phase). Next, an aqueous phase is prepared by uniformly dissolving (6) to (11) at 80° C. While stirring the oil phase at 80° C., the aqueous phase is gradually added and emulsified. The emulsion was cooled to room temperature with stirring to obtain a hair treatment.

Example 6

Hair Styling Agent

TABLE 5

| | | Blending amount (%) |
|---|---|---|
| (1) | Squalane | 12.0 |
| (2) | Amide alcohol OLH | 3.5 |
| (3) | Candelilla wax | 4.0 |
| (4) | Microcrystalline wax | 3.0 |
| (5) | Behenyl alcohol | 2.5 |
| (6) | Isostearic acid | 0.9 |
| (7) | Hydroxyethyl cellulose | 0.4 |
| (8) | Pentylene glycol | 3.0 |
| (9) | Purified water | Balance |

(1) to (6) are uniformly dissolved at 80° C. (oil phase). Next, an aqueous phase is prepared by uniformly dissolving (7) to (9) at 80° C. While stirring the aqueous phase at 80° C., the oil phase is gradually added and emulsified. The emulsion was cooled to room temperature with stirring to obtain a hair styling agent.

Example 7

Body Lotion

TABLE 6

| | | Blending amount (%) |
|---|---|---|
| (1) | Squalane | 12.0 |
| (2) | Amide alcohol OLH | 1.5 |
| (3) | Hydrogenated castor oil alcohol | 3.5 |
| (4) | Isostearic acid | 0.3 |
| (5) | Glycerin | 3.0 |
| (6) | Pentylene glycol | 1.0 |
| (7) | Ammonium Acryloyldimethyltaurate/VP Copolyme | 0.3 |
| (8) | Purified water | Balance |

(1) to (4) are uniformly dissolved at 80° C. (oil phase). Next, an aqueous phase is prepared by uniformly dissolving (5) to (8) at 80° C. While stirring the aqueous phase at 80° C., the oil phase is gradually added and emulsified. The emulsion was cooled to room temperature while stirring to obtain a body lotion.

Example 8

Emulsion Foundation

TABLE 7

| | | Blending amount (%) |
|---|---|---|
| (1) | Silicone-coated titanium oxide | 18.0 |
| (2) | Silicone-coated iron oxide(red) | 0.3 |
| (3) | Silicone-coated iron oxide(black) | 0.015 |
| (4) | Silicone-coated iron oxide(yellow) | 1.2 |
| (5) | Hydrogenated polyisobutene | 20.0 |
| (6) | Isodecyl neopentanoate | 15.0 |
| (7) | Trimethylsiloxy silicate/ decamethylcyclopentasiloxane solution | 5.0 |
| (8) | Amide alcohol OLH | 3.0 |
| (9) | 1,3-butylene glycol | 3.0 |
| (10) | Glutamic acid | 0.6 |
| (11) | Ion exchanged water | Balance |

(1) to (8) are uniformly dispersed at 80° C. (oil phase). Next, an aqueous phase is prepared by uniformly dissolving (9) to (11) at 80° C. While adding the oil phase to the aqueous phase heated to 80° C., the mixture is stirred with a disperser and emulsified. It was cooled to room temperature to obtain an emulsion foundation.

Example 9

Emollient Cream

TABLE 8

| | | Blending amount (%) |
|---|---|---|
| (1) | Behenyl alcohol | 1.0 |
| (2) | Batyl alcohol | 0.5 |
| (3) | Hydrogenated polyisobutene | 3.0 |
| (4) | Liquid paraffin | 8.0 |
| (5) | Isostearyl neopentanoate Trade name: Neolight 180P, Kokyu Alcohol Kogyo Co., Ltd. | 6.0 |
| (6) | Fragrance | Reasonable amount |
| (7) | Amide alcohol OLH | 2.0 |
| (8) | Ethyl paraben | 0.1 |
| (9) | Butyl paraben | 0.1 |
| (10) | Tocopherol | 0.5 |
| (11) | Ammonium Acryloyldimethyltaurate/VP Copolyme | 0.5 |
| (12) | Polyethylene glycol 20000 | 1.0 |
| (13) | *Crataegus cuneata* fruit extract | 0.1 |
| (14) | *Syzygium jambos* leaf extract | 0.1 |
| (15) | *Aloe* extract | 0.1 |
| (16) | *Sanguisorba officinalis* root extract | 0.1 |
| (17) | *Eugenia Caryophyllus* (clove) flower extract | 0.1 |
| (18) | *Houttuynia cordata* extract | 0.1 |
| (19) | *Althaea officinalis* root extract | 0.1 |
| (20) | *Lithospermum officinale* root extract | 0.1 |
| (21) | 1,3-butylene glycol | 3.0 |
| (22) | Glycerin | 5.0 |
| (23) | Glutamic acid | 0.4 |
| (24) | Ion exchanged water | Balance |

(11) to (24) are uniformly dissolved at 80° C. (aqueous phase). Meanwhile, (1) to (10) are uniformly dissolved at 80° C., added to the aqueous phase, and stirred at 80° C. with a disperser. After emulsification was completed, it was cooled to room temperature to obtain an emollient cream.

Example 10

Whitening Cream

TABLE 9

| | | Blending amount (%) |
|---|---|---|
| (1) | Palmitic acid | 2.0 |
| (2) | Cetyl alcohol | 1.5 |
| (3) | Vaseline | 0.5 |
| (4) | Squalane Trade name: Olive squalane, Kokyu Alcohol Kogyo Co., Ltd. | 5.0 |
| (5) | Triethylhexanoin Trade name: TOG, Kokyu Alcohol Kogyo Co., Ltd. | 3.0 |
| (6) | Hexyl laurate Trade name: KAK HL, Kokyu Alcohol Kogyo Co., Ltd. | 2.0 |
| (7) | Amide alcohol OLH | 2.5 |
| (8) | Fragrance | 0.1 |
| (9) | Tranexamic acid | 2.0 |
| (10) | Glutamic acid | 0.5 |
| (11) | Ammonium Acryloyldimethyltaurate/VP Copolyme | 0.5 |
| (12) | Xanthan gum | 0.1 |
| (13) | Methyl paraben | 0.1 |
| (14) | Phenoxyethanol | 0.1 |
| (15) | Glycerin | 3.0 |
| (16) | *Hypericum perforatum* extract | 0.1 |
| (17) | *Melilot* extract | 0.1 |
| (18) | Royal jelly extract | 0.1 |
| (19) | Ion exchanged water | Balance |

(9) to (19) are uniformly heated at 80° C. (aqueous phase). Next, the oil phase of (1) to (8) is uniformly dissolved at 80° C. The oil phase heated to 80° C. is added to the aqueous phase heated to 80° C., and the mixture is stirred with a homomixer and emulsified. Upon completion of the emulsification, it was cooled to room temperature to obtain a whitening cream.

Example 11

Oil-in-Water Emulsion Sunscreen

TABLE 10

| | | Blending amount (%) |
|---|---|---|
| (1) | Octyl p-methoxycinnamate | 6.0 |
| (2) | Glyceryl octyl di-p-methoxycinnamate | 2.0 |
| (3) | 4-tert-buty-4'-methoxydibenzoylmethane | 2.0 |
| (4) | Tetra(octanoate/p-methoxycinnamate)pentaerythritol | 3.0 |
| (5) | Ethylhexyl isononanoate Trade name: ES108109, Kokyu Alcohol Kogyo Co., Ltd. | 12.0 |
| (7) | Squalane Trade name: Olive squalane, Kokyu Alcohol Kogyo Co., Ltd. | 6.0 |
| (8) | Amide alcohol OLH | 3.0 |
| (9) | Microcrystalline wax | 0.1 |
| (10) | Fragrance | 0.1 |
| (11) | Ion exchanged water | Balance |
| (12) | Dipropylene glycol | 5.0 |
| (13) | Methyl paraben | 0.2 |
| (14) | Ammonium Acryloyldimethyltaurate/VP Copolyme | 0.3 |
| (15) | Glutamic acid | 0.6 |

(11) to (15) are uniformly dissolved at 80° C. (aqueous phase). Next, the oil phase of (1) to (10) is uniformly dissolved at 80° C. The oil phase at 80° C. is added to the aqueous phase heated to 80° C. and stirred with a disperser. Upon completion of the emulsification, it was cooled to room temperature to obtain an oil-in-water emulsion sunscreen.

INDUSTRIAL APPLICABILITY

It is possible to provide a conditioning agent and a conditioning composition which have high adsorptivity to fibers, hair and skin and give smoothness thereto.

The invention claimed is:

1. A conditioning composition comprising an organic acid and the amide alcohol:

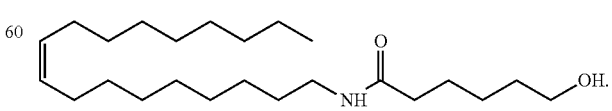

2. The composition according to claim 1, comprising: 0.1 to 10.0 mass % of the amide alcohol, and 0.1 to 10.0 mass % of the organic acid.

3. The composition according to claim 1, wherein the molar ratio of the amide alcohol to the organic acid is from 2:1 to 1:1.

4. The composition according to claim 1, wherein the organic acid is one or more selected from the group consisting of a monocarboxylic acid, a dicarboxylic acid, a hydroxycarboxylic acid, a polycarboxylic acid, an acidic amino acid, and a fatty acid.

5. The composition according to claim 1, comprising one or more oil agents selected from the group consisting of ester oils, silicone oils, and hydrocarbon oils.

6. The composition according to claim 5, which is an O/W emulsion composition.

7. The composition according to claim 6, which is free of surfactant.

8. The composition according to claim 1, comprising glutamic acid as organic acid.

9. The composition according to claim 5, comprising one or more selected from the group consisting of squalane, liquid paraffin, and nonvolatile hydrocarbon oil as an oil agent.

10. The composition according to claim 1, which is a hair and/or skin cosmetic.

\* \* \* \* \*